US005265786A

United States Patent [19]
Heimerl et al.

[11] Patent Number: 5,265,786
[45] Date of Patent: Nov. 30, 1993

[54] APPARATUS FOR PLACING SURGICAL STAPLES

[75] Inventors: Albert Heimerl; Holger Kartheus, both of Hamburg; Dietmar Paske, Buxtehude; Hans-Ulrich Plenio, Hamburg, all of Fed. Rep. of Germany

[73] Assignee: Beiersdorf AG, Hamburg, Fed. Rep. of Germany

[21] Appl. No.: 938,615

[22] Filed: Sep. 1, 1992

[30] Foreign Application Priority Data

Oct. 11, 1991 [DE] Fed. Rep. of Germany ....... 4133692

[51] Int. Cl.$^5$ ............................................. A61B 17/068
[52] U.S. Cl. ........................................ 227/175; 227/19
[58] Field of Search ........................... 227/19, 175, 120

[56] References Cited

U.S. PATENT DOCUMENTS

| 4,411,378 | 10/1983 | Warman | 227/19 |
| 4,470,532 | 9/1984 | Froehlich | 227/19 |
| 4,645,111 | 2/1987 | Larrabee et al. | 227/19 |
| 4,664,305 | 5/1987 | Blake, III et al. | 227/19 |
| 4,669,647 | 2/1987 | Storace . | |
| 5,080,275 | 1/1992 | Heimerl et al. | 227/19 |

*Primary Examiner*—Scott A. Smith
*Attorney, Agent, or Firm*—Dvorak and Traub

[57] ABSTRACT

An apparatus for placing surgical staples which are moved one after another from a staple support onto a lower die and are deformed there using an upper die, by lowering and further adjusting the upper die onto the particular staple to be placed situated on the lower die, wherein the staple is deformed by bending around the lower die and then separated from the lower die using an ejector, is described. A particularly simple and function-safe design for the ejector system is produced in that the ejector can be displaced in a straight line and is brought to rest against the limbs of the implanted staple by means of a head below the lower die when adjusting to its second position.

6 Claims, 4 Drawing Sheets

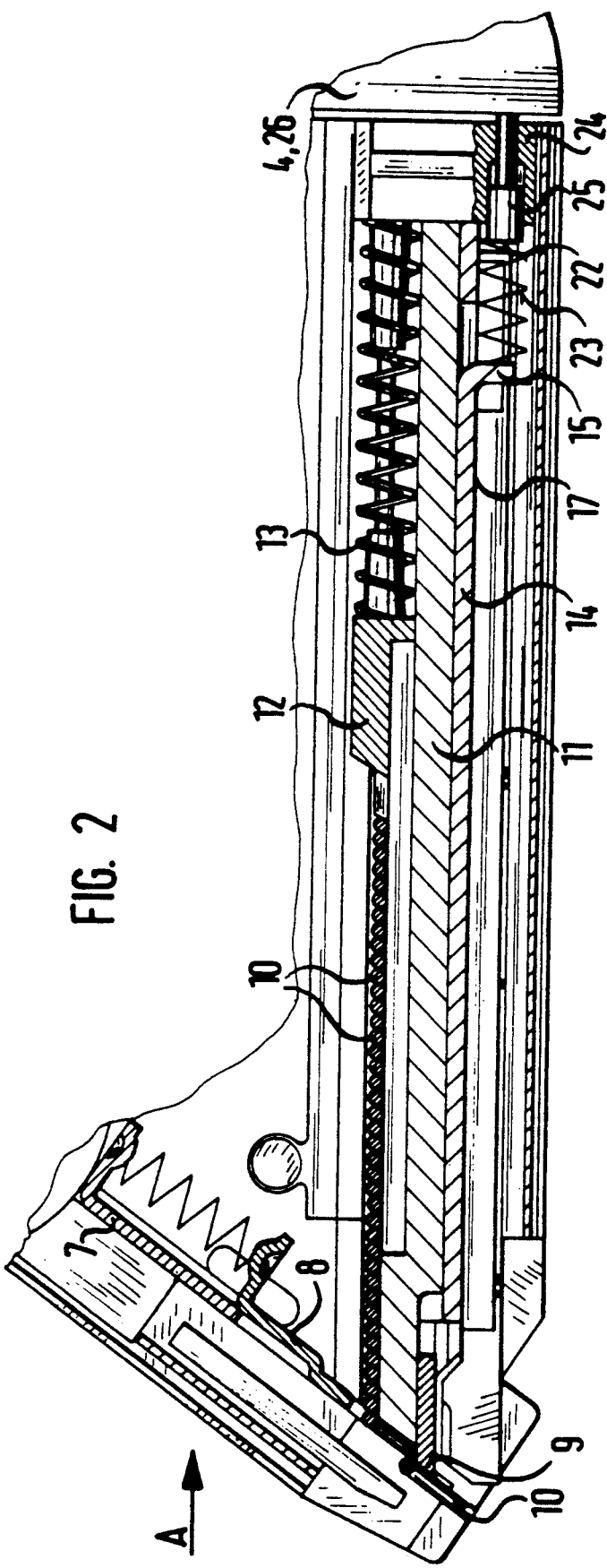

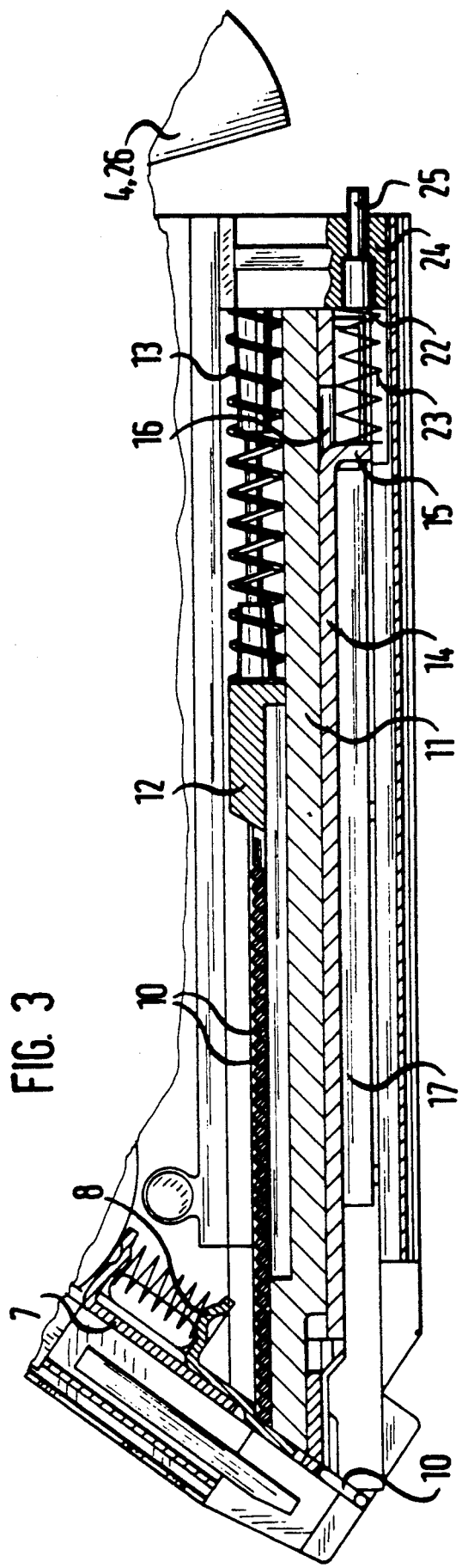

APPARATUS FOR PLACING SURGICAL STAPLES

BACKGROUND OF THE INVENTION a) Field of the Invention

The invention relates to an apparatus for placing surgical staples which can be moved one after another from a staple support onto a lower die and can be deformed there using an upper die, by being able to lower and further adjust the upper die onto the particular staple to be placed situated on the lower die, wherein the staple is deformed by bending around the lower die and then separated from the lower die using an ejector which stands in a first position during the deformation process when it is not in contact with the particular staple to be implanted, and which can be moved into a second position in the direction of the implanted staple after the deformation process to push the staple from the lower die.

b) Description of the Prior Art

In known surgical staplers (U.S. Pat. No. 3,873,016, U.S. Pat. No. 4,109,844, U.S. Pat. No. 4,202,480) it is often necessary for the surgeon to move the apparatus a certain distance forwards or backwards after implanting a staple to thus release the staple from the lower die. However, this measure disturbs many surgeons because the horizontal movement of the apparatus required for this is in the opposite direction to the mainly vertical course of movement usual for staples.

Apparatus for which the surgeon need only concentrate on the precise placing of the staples during use and is not distracted further by movements of the apparatus which are also required for ejecting the particular implanted staple from the lower die, is therefore preferred. Apparatus of this type may be easily lifted vertically from the wound after placing a staple, when the staple has been ejected automatically from the apparatus or from the lower die.

An apparatus is known from European patent 0 124 556, the lower die of which can be mechanically adjusted so that after placing a staple it is withdrawn from the region between staple bar and wound, wherein the staple moves away from the lower die and is released. However, this apparatus has complicated and troublesome mechanics. A movable lower die also has the disadvantage that the precision of staple deformation required is no longer possible even at the lowest and mostly unavoidable deviations of the actual position of the lower die from its theoretical position relative to the upper die.

A further possibility for releasing the staple from the lower die is described in European application 0 324 166. In this previously known apparatus, a leaf spring serving as ejector presses constantly on the bar of the staple to be implanted and implanted staple, so that the leaf spring pushes the staple from the lower die as soon as the upper die is removed from its position with the staple. However, this solution has the disadvantage that forces act on the staple to be placed as a result of the ejector leaf spring even before and during the staple deformation, and these forces may lead to the staple being adjusted, for example by tilting from its intended position and then it is no longer possible to implant it in an exactly aligned position. It will therefore be necessary to guide the staples in several planes by means of additional precision components, and this is associated with a correspondingly high effort.

To this end an improvement will be an apparatus in which the ejector in a first position does not contact the particular staple to be implanted before and during the deformation process, and which can be adjusted into a second position in the direction of the implanted staple after deformation of the staple to push or eject the staple from the lower die.

In a known apparatus of this type (U.S. Pat. No. 4,523,707), the ejector is adjusted between two positions on an arc-shaped path, wherein it is laterally displaced into the second position mentioned when moving-in to thus bring ejector tools to rest against the staple situated on the lower die. However, the movement of the ejector on a curved path and the displacement movement of the ejector tools which is lateral relative to the curved path necessitate complex designs and troublesome control and adjustment mechanisms for the ejector. Since tools thereof engage at the staple bar, there are also unfavourable leverages in the region between the surfaces of the wound to be stapled and the lower die, so that there may be excessive tilting during the ejection process and hence undesirable movements of the staple in the tissue.

In contrast the invention is to propose an apparatus, the ejector system of which operates according to a simple, reliable and inexpensive principle and by means of which the staple may be pushed without difficulty and without a tendency to tilt from the lower die.

SUMMARY OF THE INVENTION

To this end, according to the present invention, there is provided apparatus for placing surgical staples which can be moved one after another from a staple support onto a lower die and can be deformed there using an upper die, by being able to lower and further move the upper die onto the particular staple to be placed situated on the lower die, wherein the staple is deformed by bending around the lower die and then separated from the lower die using an ejector which stands in a first position during the deformation process when it is not in contact with the particular staple to be implanted, and which can be moved into a second position in the direction of the implanted staple after the deformation process to push the staple from the lower die, characterised in that the ejector can be moved on a straight path and can be brought to rest against the limbs of the implanted staple by means of a head below the lower die when moving to its second position.

The straight path of movement of the ejector places low requirements in terms of construction on the designs and the adjusting mechanism of the ejector. If this lower half of the lower die is brought to rest against the staple limbs, a favourable point of application between ejector and staple results therefrom, since this point of application is situated between the surface of the tissue and the region where the staple bar lies on the lower die. This prevents the staple from tilting and thus moving in the tissue when ejecting the staple from the lower die. In addition, the staple bar experiences no force component in the direction of the lower die, so that the staple bar is moved away from the lower die essentially without friction.

Preferably, the head of the ejector has a transverse bar which is longer than the distance between the staple limbs in order to be able to bring it safely to rest against both limbs of the staple. Advantageously, the head is designed as a flat T shape and the transverse bar formed by the free end of the T shape is correspondingly longer than the distance between the staple limbs.

Hand-actuated apparatus for placing surgical staples have in most cases a first grip which may be pivoted out from a rest position against a fixed second grip to actuate the apparatus. According to a further preferred embodiment of the invention, an apparatus of this type may have an axially movable ram, on one end of which a cam of the first grip situated in the rest position or reverting to this position acts, and the other end of which contacts the ejector.

Moreover, the staple support is advantageously supported by a fixed, bent support element stamped from sheet metal, the distal end of which forms the lower die and which has a stop lying at the same level as the stop on the ejector, wherein a spring is mounted between both stops and attempts to constantly press the ejector in the direction of its first position, and wherein the stop situated on the ejector cooperates with the ram on its side facing away from the spring.

Preferably, the ram guided in a wall of the apparatus housing should project freely outwards from this wall over a part of its length and be situated there in the pivoting plane of a cam arranged on the first grip, so that the ram and hence also the ejector can be moved and controlled as a function of the position of the first grip.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

FIG. 2 shows a longitudinal section through the lower region of the apparatus according to FIG. 1 on a larger scale and with the ejector situated in the second position, FIG. 3 shows a representation corresponding to FIG. 2, but with the ejector situated in the first position.

Figure 1:
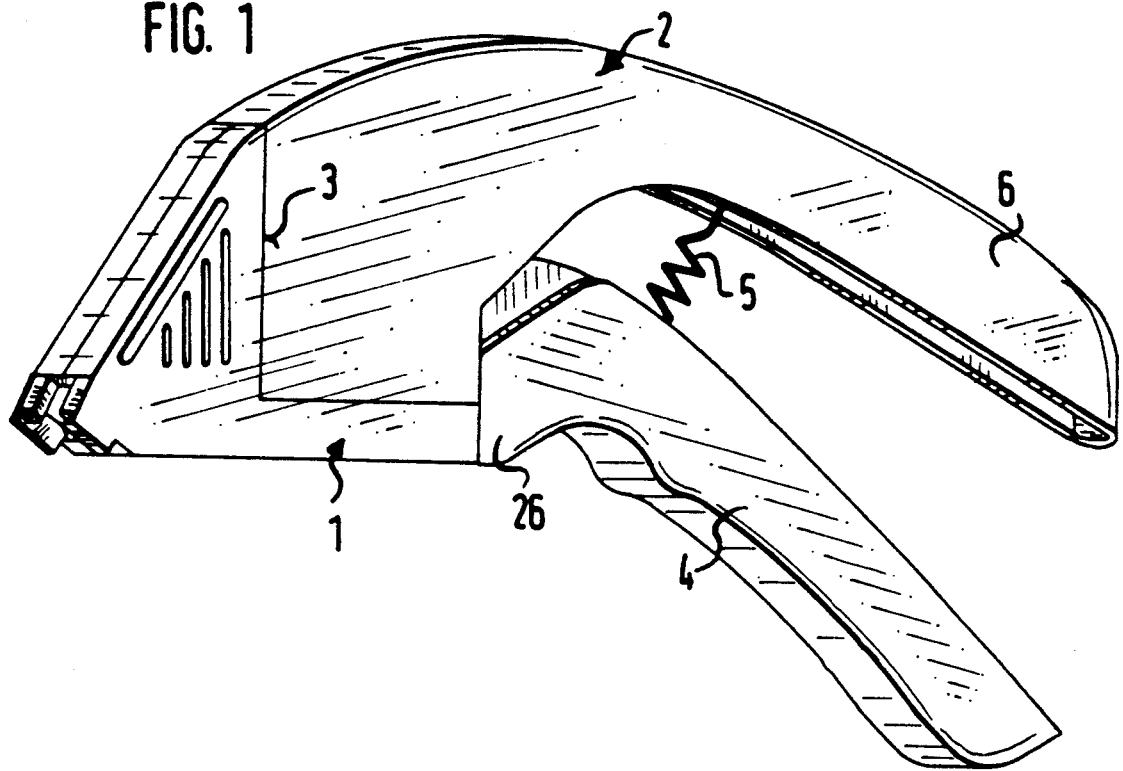
FIG. 1 shows a perspective representation of an apparatus according to the invention.

The apparatus consists essentially of two apparatus parts 1, 2, the housings of which rest against one another at the separation plane 3. A first grip 4 belonging to the apparatus part 2 and which may be pivoted out of its rest position shown in FIGS. 1 and 2 against a pressure spring 5 shown schematically in the direction of a fixed second grip 6 likewise belonging to the apparatus part 2, in order to actuate parts situated in removable apparatus part 1 to implant a staple.

Figure 4:
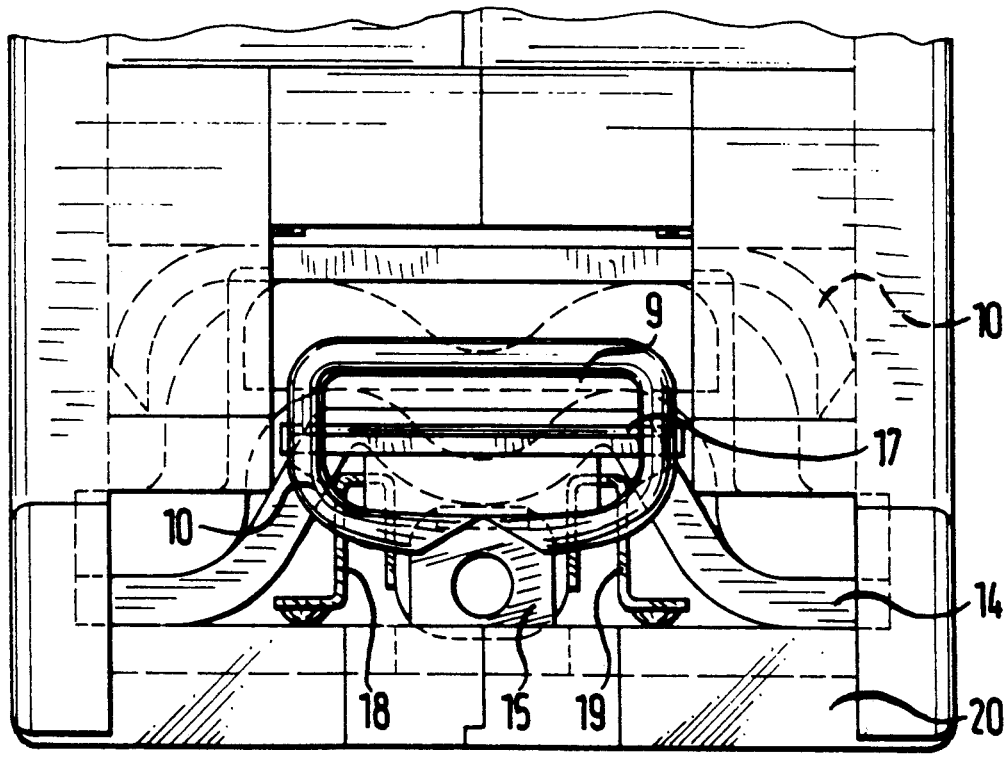
FIG. 4 shows an end view of the apparatus seen in the direction of arrow A in FIG. 2, wherein some parts of the apparatus are omitted for a better view of other parts of the apparatus.
Figure 5:
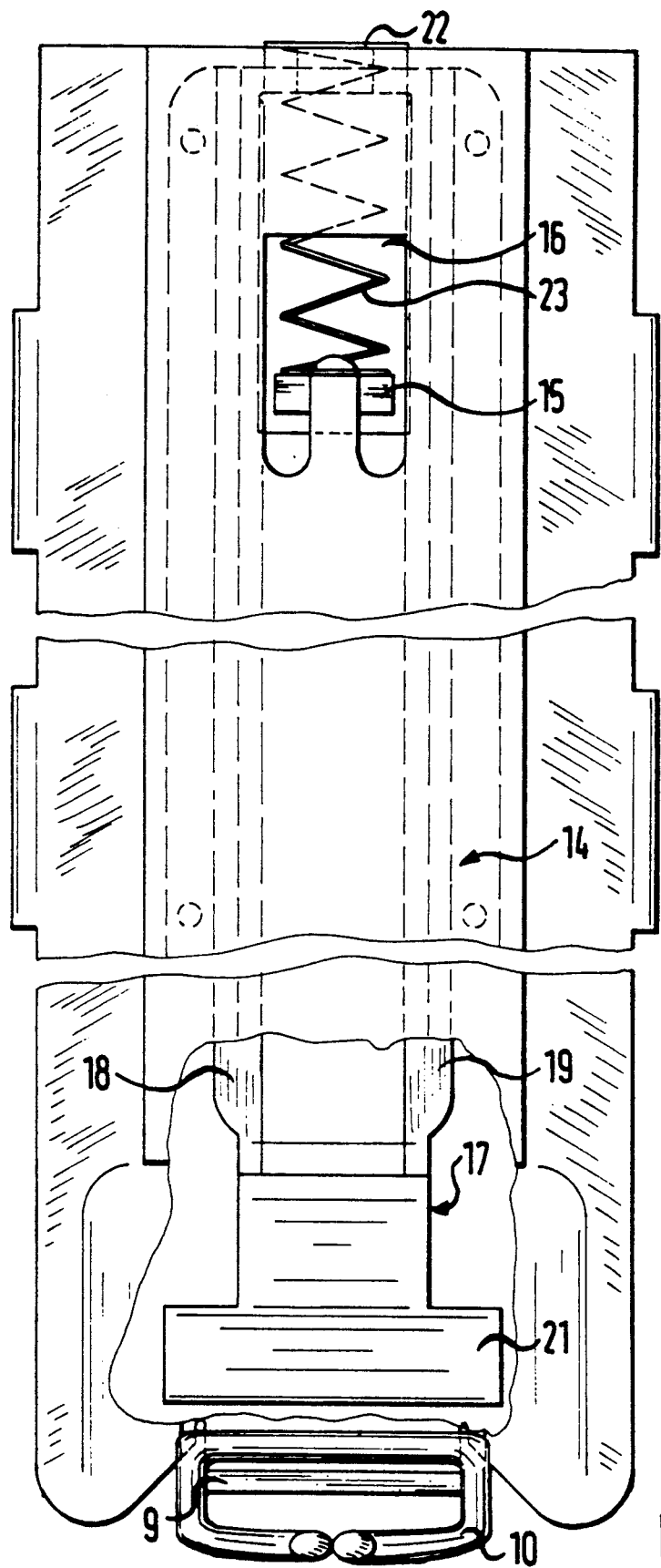
FIG. 5 shows a plan view of the ejector and some parts cooperating with the latter.

These parts are, inter alia, an upper die 7 and a pressure pad 8 which may be adjusted from an upper position (FIG. 2) in the direction of a lower die 9 by means of their ends by actuating the grip 4, in order to fix the particular staple 10 situated on the lower die using the pressure pad and to deform it by bending around the lower die using the upper die, wherein the staple shape shown in FIGS. 4 and 5 is produced.

The subsequent staples 10 are situated on a staple support 11 and are constantly pressed distally in the direction of the operating plane of the upper die 7 and of the pressure pad 8 using a staple drive 12 guided on the staple support and having a pressure spring 13, so that the staples may be moved one after another on the lower die 9 and deformed there using the upper die 7.

The construction of the apparatus given in this respect and the tasks and functions of the aforementioned and other parts have also been shown and described in detail in German Offenlegungsschrift 3 934 698, so that in this connection further details become unnecessary in the light of this publication.

The staple support 11 is supported by a bent support element 14 stamped from sheet metal, the distal end of which forming the lower die 9 and a downwardly angled stop 15 being provided there which engages a recess 16 of an ejector 17.

This ejector stands on a lower housing wall 20 of the apparatus part 1 by means of legs 18, 19 and slides so as to be longitudinally movable, that is can be moved to the left and right on a straight path in accordance with FIGS. 2 and 3, guided below the staple support 11 and the support element 14, wherein guiding is provided by appropriate shaping of the parts of the ejector 17 directed upwards and of the lower contour of the support element 14 situated next to these parts, as can be seen in FIG. 4.

The head 21 forming the distal end of the ejector 17 is designed as a T shape, the transverse bar of which is longer than the distance between the limbs of a deformed staple 10, so that the ejector head or transverse bar passes to rest securely against the staple limbs below the lower die 9 and may push the staple from the lower die, as is also described in more detail below.

At the opposite end the ejector 17 has an upwardly angled stop 22 which lies at the same level as the stop 15 on the fixed support element 14, so that a pressure spring 23, which attempts to constantly press the ejector in the direction of its first position when in each case it does not contact the staple lying on the lower die, may be mounted between both stops (FIG. 3).

One end of a ram 25 guided to be axially movable in the rear housing wall 24 rests on the rear-side surface of the stop 22, that is facing away from the spring 23, which ram 25 projects outwardly from the housing wall 24 at its other end over a part of its length and is situated there in the pivoting plane of a cam 26 designed on the grip 4.

For a non-actuated apparatus, the apparatus parts occupy the positions shown in FIGS. 1 and 2. If the apparatus is actuated against the grip 6 by pivoting the grip 4, initially the cam 26 is raised from the ram 25, after which the latter has moved to the right by a short distance starting from its position according to FIG. 2, since the spring 23 likewise presses the ejector 17 to the right into the retracted first position and thus the stop 22 brings the ram 25 into its other end position according to FIG. 3.

After the head 21 is removed in this manner from the path of movement of the upper die 7 and pressure pad 8 and from the region of the lower die 9 by adjusting the ejector 17, the upper die 7 is adjusted downwardly onto the lower die 9 by continued pivoting of the lever 4 and while catching the particular foremost staple 10 by means of the pressure pad 8 in order to finally deform and to implant the staple in known manner.

If subsequently the grip 4 is released manually and reverts back to its rest position under the influence of the spring 5, the upper die 7 and the pressure pad 8 are put back upwards into their starting position and the cam 26 will come to rest against the ram 25 towards the end of this gripping movement in order to bring the latter together with the ejector 17 to the left back into the second possible position according to FIG. 2 at a tension for the spring 23 which is then becoming greater. The ejector head 21 thus moves against the limbs of the implanted staple 10 projecting downwards in the course of movement of the ejector 17 until finally this staple is pushed completely from the lower die 9, as shown in FIG. 2.

These processes proceed automatically to complete separation of the implanted staple from the apparatus with an appropriate design of the spring 5, so that the surgeon simply only needs to open the hand operating the apparatus to release an implanted staple. Moreover, the ejector is situated on the lower die during the movement of the staple to be placed and also during the implanting of a staple in its retracted first position in each case, and accordingly not in contact with the staple, so that the ejector is thus unable to exert any other interfering forces on the staple.

The mechanical means shown and described for adjusting the ejector from one to the other position represent a simple and function-safe solution. However, the ejector could also be adjusted by means of other movable parts of the apparatus with and against the action of a spring. Moreover, the invention can be realised not only for hand-actuated apparatus, but also for apparatus with electrical or other drives for the tools deforming the staples.

The present invention may be embodied in other specific forms without departing from the spirit or essential attributes thereof and, accordingly, reference should be made to the appended claims rather than to the foregoing specification as indicating the scope of the invention.

We claim:

1. In an apparatus for placing surgical staples which are provided with two limbs connected by a bar, which staples can be moved one after the other from a staple support onto a lower die and can be deformed there by an upper die and by lowering the upper die onto the particular staple to be placed and situated on the lower die, wherein the staple is deformed by bending around the lower die and then separated from the lower die by using an ejector which, during the deformation process, stands in a first position out of contact with the particular staple to be implanted and which can be moved into a second position in the direction of the implanted staple after the deformation process to push the staple from the lower die, the improvement comprising a lower housing wall, one end of said ejector being provided with a head to engage with limbs of the implanted staple below said lower die when the ejector is moved into the second position, and means extending from under said ejector for movably supporting said ejector on said lower housing wall for movement along a straight path.

2. Apparatus according to claim 1, characterized in that the head of the ejector has a transverse bar which is longer than the distance between the staple limbs.

3. Apparatus according to claim 1, wherein the head of the ejector is designed as a flat T-shaped piece forming a transverse bar which is longer than the distance between the staple limbs.

4. Apparatus according to claim 1, wherein the staple support is supported by a fixed, bent support element stamped from metal sheet, the distal end of which forms the lower die and which has a stop lying at the same level as a stop on the ejector, a spring mounted between both stops is constantly pressing the ejector in the direction of the ejector's first position, and the stop situated on the ejector cooperates with a side of the ram, which side faces away from the spring.

5. Apparatus according to claim 1, having a first grip which can be pivoted out from a rest position in direction of a stationary second grip to actuate the apparatus, characterized by an axially movable ram, and further characterized in that a cam of the first grip acts against one end of the ram when the first grip is in the rest position or reverts to the rest position, and that the other end of the ram acts against the ejector.

6. Apparatus according to claim 5, wherein the ram is slidably supported in a wall of a housing and partly projects freely outwards from said wall and is situated in a pivoting plane of a cam arranged on the first grip.

* * * * *